US005830905A

United States Patent [19]
Diana et al.

[11] Patent Number: 5,830,905
[45] Date of Patent: Nov. 3, 1998

[54] COMPOUNDS, COMPOSITIONS AND METHODS FOR TREATMENT OF HEPATITIS C

[75] Inventors: Guy D. Diana, Pottstown; Thomas R. Bailey, Phoenixville; Theodore J. Nitz, Pottstown, all of Pa.

[73] Assignee: Viropharma Incorporated, Malvern, Pa.

[21] Appl. No.: 625,718

[22] Filed: Mar. 29, 1996

[51] Int. Cl.⁶ ........................ A61K 31/445; C07D 401/06
[52] U.S. Cl. ........................ 514/322; 546/184; 546/186; 546/187
[58] Field of Search ........................ 424/422; 546/184, 546/186, 187; 514/322

[56] References Cited

U.S. PATENT DOCUMENTS 5,633,388   5/1997   Diana et al. ........................ 548/305.7

OTHER PUBLICATIONS

Choo et al., "Isolation of a cDNA Clone Derived from a Blood–Borne Non–A, Non–B Viral Hepatitis Genome," *Science*, 244:359–362 (1989).

Lain et al., "RNA Helicase: a Novel Activity Associated with a Protein Encoded by a Positive Strand RNA Virus," *Nucleic Acids Res.* 18:7003–7006 (1991).

Warrener et al., "Pestivirus NS3 (p80) Protein Possesses RNA Helicase Activity," *J. Virol.* 69:1720–1726 (1995).

Kim et al., "Rapid Isolation of Cell–Type Specific Protein Tyrosine Kinases by Degenerate Polymerase Chain Reaction Combined with Differential Hybridization Technique," *Biochem. Biophys. Res. Comm.* 214:60–68 (1995).

McConnaughie et al., "Design and Synthesis of RNA–Specific Groove–Binding Cations: Implications for Antiviral Drug Design," *J. Med. Chem.* 37:1063–1069 (1994).

*Primary Examiner*—Michael P. Woodward
*Assistant Examiner*—Brenda G. Brumback
*Attorney, Agent, or Firm*—Dann, Dorfman, Herrell and Skillman

[57] ABSTRACT

Derivatives of piperidine are useful in prophylaxis and treatment of hepatitis C virus infections.

17 Claims, No Drawings

COMPOUNDS, COMPOSITIONS AND METHODS FOR TREATMENT OF HEPATITIS C

FIELD OF THE INVENTION

The present invention relates to compounds, compositions and methods for the treatment of hepatitis C virus (HCV) infection. In particular, the present invention provides novel piperidine derivatives, pharmaceutical compositions containing such compounds and methods of using the compounds in treating HCV and other viral diseases.

BACKGROUND OF THE INVENTION

HCV, which is found in all parts of the world, has been characterized as single-stranded RNA virus of about 9.5 kilobases in length. Choo et al., Science, 244: 395-62 (1989).

Surgery patients and others requiring blood transfusions, and especially those having suppressed immune systems, resulting, for example, from drugs administered in connection with organ transplantation, are at risk of developing HCV infection, which is the primary cause of transfusion-associated hepatitis in the world today. It has been estimated that posttransfusion hepatitis C may be responsible for up to 3,000 annual cases of chronic active hepatitis or cirrhosis of the liver in the U.S. alone. Hemodialysis patients, as well as intravenous drug abusers are other groups which are at risk for acquiring HCV infection.

The mechanism by which HCV replicates has not been thoroughly elucidated, thus hindering research aimed at developing an effective vaccine. Immune globulin has been reported for prophylaxis of transfusion-associated viral hepatitis. However, the Centers for Disease Control do not presently recommend immune globulin for this purpose.

Various clinical studies have been conducted with the goal of identifying pharmaceutical agents capable of effectively treating HCV infection in patients afflicted with chronic hepatitis C. These studies have involved the use of dideoxy-nucleoside analogues and interferon-alpha, alone and in combination therapy with other anti-viral substances. Such studies have shown, however, that substantial numbers of the participants do not respond to this therapy, and of those that do respond favorably, a large proportion were found to relapse after termination of treatment.

Thus, a need exists for new anti-viral agents and treatments for HCV infection that overcome the limitations of existing pharmaceutical therapies. Insofar as is known, piperidine derivatives of the type described herein have not been previously reported as being useful for the treatment of HCV.

SUMMARY OF THE INVENTION

In accordance with one aspect, the present invention provides compounds, including isomers, having the following structure:

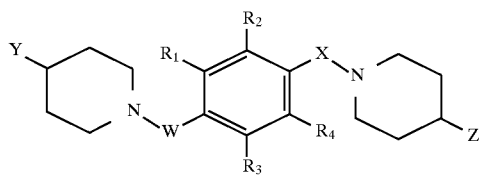

in which $R_1$, $R_2$, $R_3$ and $R_4$ are the same or different and represent substituents selected from the group consisting of hydrogen, alkyl ($C_1$–$C_6$) halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; W and X represent the same or different linking moieties selected from the group consisting of alkylene ($C_1$–$C_5$) and carbonyl (—(C=O)—); Y and Z represent the same or different substituents selected from the group consisting of

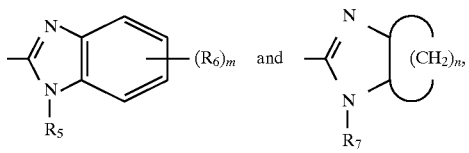

in which $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and in which $R_7$ represents a substituent selected from the group consisting of hydrogen, alkyl and acyl, and n is from 3 to 5, and the isomers and pharmaceutically acceptable salts of those compounds.

In accordance with another aspect, the present invention provides a class of intermediates which are useful in preparing compounds of formula I, above. The intermediates of the invention have the structure:

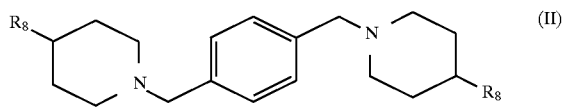

in which $R_8$ represents a carbalkoxy ($C_1$–$C_6$) substituent or

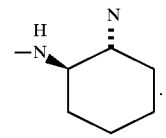

According to still another aspect, the present invention provides pharmaceutical compositions comprising one or more of the above-described piperidine derivatives in combination with a pharmaceutically acceptable carrier medium.

In accordance with yet another aspect, the present invention provides a method for treating viral hepatitis C infections in mammalian hosts by administering an effective amount of the compounds of the invention to a patient susceptible to hepatitis C infection or suffering from such an infection.

DETAILED DESCRIPTION OF THE INVENTION

The compounds of the invention can be conveniently prepared from known starting materials according to reactions described in the examples.

In vitro studies demonstrating the usefulness of the compounds of the invention as anti-viral agents have been performed. Anti-viral activity was measured on the basis of inhibition of helicase activity. The biological studies of the anti-viral activity of the compounds of the invention are described below.

The term "alkyl" as used herein refers to aliphatic hydrocarbon radicals of one to six carbon atoms in length. Similarly, the term "alkyl", or variations thereof, used in combination form to name substituents such as carbalkoxy, alkoxy, alkylthio, alkylamino, alkylsulfinyl or alkylsulfonyl also refers to aliphatic hydrocarbon radicals of one to six carbon atoms in length, and preferably of one to four carbon atoms in length.

Among the particularly preferred embodiments of the invention are compounds, including isomeric forms, having the formula:

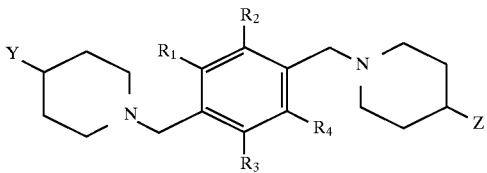

in which $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; Y and Z represent the same or different substituent selected from the group consisting of

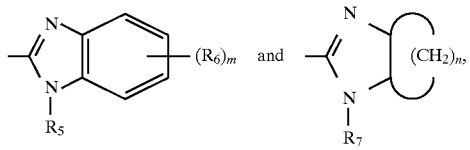

in which $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and in which $R_7$ represents a substituent selected from the group consisting of hydrogen, alkyl and acyl, and n is from 3 to 5, and the pharmaceutically acceptable salts of such compounds.

Also preferred are compounds, including isomeric forms, having the formula:

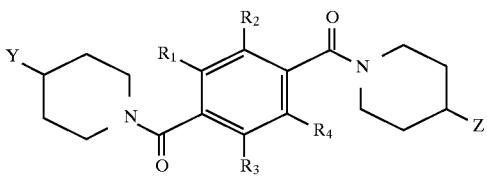

in which $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; Y and Z represent the same or different substituent selected from the group consisting of

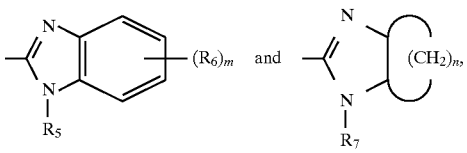

in which $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and wherein $R_7$ represents a substituent selected from the group consisting of hydrogen, alkyl and acyl, and n is from 3 to 5, and the pharmaceutically acceptable salts of this compound.

Isomers of the above-described compounds such as those in which the piperidine moieties are in the meta- or para-position relative to one another on the central phenylene nucleus may be used in practicing the invention.

As previously noted, the compounds of formula I, above, including their pharmaceutically acceptable salts, exhibit antiviral activity against hepatitis C virus.

The compounds of the invention can form salts with inorganic and organic acids, including, for example, acids such as hydrochloric acid, hydrobromic acid and methanesulfonic acid.

The pharmaceutically acceptable salts of the compounds of formulas I and II are prepared following procedures which are familiar to those skilled in the art.

The antiviral pharmaceutical compositions of the present invention comprise one or more of the compounds of formula I, above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa, 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.5% and not more than 90% by weight based on the total weight of the composition, including carrier medium and/or auxiliary agent(s). Preferably, the proportion of active agent varies between 5%–50% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The compounds of the invention may be administered using any amount and any route of administration effective for attenuating infectivity of the hepatitis C virus. Thus, the expression "therapeutically effective amount", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like. The anti-hepatitis C compounds are preferably formulated in dosage unit form for ease of administration and uniformity of dosage. Dosage unit form as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium. Typically, the anti-viral compounds of the invention will be administered in dosage units containing from about 1 mg to about 500 mg of the anti-viral agent by weight of the composition with a range of about 1 mg to about 50 mg being preferred.

The compounds of the invention may be administered orally, parenterally, such as by intramuscular injection, intraperitoneal injection, intravenous infusion or the like, depending on the severity of the infection being treated. The compounds of the invention may be administered orally or parenterally at dosage levels of about 0.1 to about 50 and preferably from about 1 to about 10 mg/kg, of patient body weight per day, one or more times a day, to obtain the desired therapeutic effect.

Although the piperidine derivatives can be administered to any patient which is susceptible to hepatitis C infection, the compounds are intended for the treatment of mammalian hosts, and especially humans.

The compounds of the invention will typically be administered from one to four times a day so as to deliver the above-mentioned daily dosage. However, the exact regimen for administration of the compounds and compositions described herein will necessarily be dependent on the needs of the individual patient being treated, the type of treatment administered and the judgment of the attending physician.

In view of the inhibitory effect on helicase enzyme activity produced by the compounds of the invention, it is anticipated that these compounds will be useful not only for therapeutic treatment of infection, but for hepatitis C viral prophylaxis, as well. The above-noted dosages will be essentially the same whether for treatment or prophylaxis of hepatitis C infection.

The following examples are provided to describe the invention in further detail. These examples, which set forth the best mode presently contemplated for carrying out the invention, are intended to illustrate and not to limit the invention.

Examples 1 to 5 illustrate the chemical synthesis of the compounds of the invention.

EXAMPLE 1
Preparation of 1,1'-[1,4-phenylene bis(methylene)]bis(4,4'-carboxyethoxy)piperidine A suspension of 5.0 g (18.0 mmol) of 4-dibromoxylene, 6.0 g (37.8 mmol) of ethyl isonipecotate, and 6.5 g (57.0 mmol) of milled potassium carbonate in 100 ml of ethanol was refluxed under nitrogen for 16 hours. The suspension was cooled to room temperature, and then filtered. The filtrate was concentrated in vacuo to provide 10 g of the crude product as a white solid. Recrystallization from ethyl acetate/hexanes yielded 7.0 g (89% yield) of the product as a white solid with a melting point of 72°–74°.

EXAMPLE 2
Preparation of 1,1'-[1, 4-phenylenebis(methylene)]bis (4,4'-(N,N'-trans-2-aminocyclohexyl)carboxamido)piperidine A suspension of 1.12 g (2.7 mmol) of 1,1'- [1,4-phenylene bis(methylene)]bis(4,4'-carboxyethoxypiperidine in 20 ml of trans-1,2-diaminocyclohexane was refluxed under nitrogen for 22 hours. Upon cooling, a white precipitate was recovered by filtration, and washed with ether followed by water. After drying under vacuum at 50° C. for 16 hours, there was recovered 0.57 g (38% yield) of the product as a fine, white solid with a melting point greater than 250° C.

EXAMPLE 3
Preparation of 1,1'-[1,4-phenylenebis (methylene)]bis(4,4'-trans-(4,5,6,7,8,9-hexahydro)benzimidazoyl)piperidine A mixture of 0.50 g of 1,1'-[1,4-phenylenebis (methylene)]bis(4,4'-(N,N'-trans-2-aminocyclohexyl) carboxamido) piperidine and 1.2 g of phosphorous oxybromide was heated at 150° C. for 30 minutes. Upon cooling to room temperature, the light orange solid was dissolved in ice water, and the aqueous solution basified to pH 9 with 10% NaOH solution. The tan solid was recovered by filtration yielding 53 mg (11% yield) of the crude product after drying in vacuo. The crude product was dissolved into 25 ml of ethanol, and the solution treated with 0.5 ml (excess) 1.0 M ethereal HCl The precipitate was recovered by filtration, and dried in vacuo affording 51 mg of tetrahydrochloride salt as a tan powder with a melting point greater than 250° C.

EXAMPLE 4
Preparation of 1,1'-[1,4-phenylenebis (methylene)]bis(4,4'-benzimidazoyl) piperidine A suspension of 1.00 g (2.4 mmol) of 1,1'-[1,4-phenylene bis(methylene)]bis(4,4'-carboxyethoxypiperidine and 0.52 g (4.8 mmol) of o-phenylenediamine was refluxed in 40 ml of 6N HCl for 5 days. Upon cooling, the green homogeneous solution was basified to pH 8 with solid NaOH and the precipitate recovered by filtration. The pink solid was washed with water and dried in vacuo for 12 hours, yielding 0.477 g of the crude product as a pink solid. The crude product was suspended in 3 mL of phosphorous oxychloride and heated in a sealed tube at 150° C. for 4 hours. Upon cooling, the slurry was poured over ice and the green solution filtered through Solka Floc. The filtrate was basified with solid NaOH and the tan precipitate was collected by filtration. The filter cake was washed with water and dried in vacuo at 80° C. for 14 hours to provide 0.269 g (22% yield) of the product as a pink/tan powder with a melting point greater than 250° C.

EXAMPLE 5
Preparation of 1,1'-[1,4-phenylenebis (carbonyl)]bis(4,4'-benzimidazoyl) piperidine A suspension of 1.00 g (5.0 mmol) 4-(benzimidazole) piperidine, 0.508 (2.5 mmol) of terephthaloyl chloride and 1.45 mL (11.2 mmol) of diisopropylethylamine in 15 mL of dry dimethylformamide was allowed to stir at room temperature under nitrogen for 16 hours. The mixture was diluted with 20 mL of water and the precipitate was collected by filtration and washed with water.

Drying in vacuo at 40° C. provided 0.869 g (46% yield) of the product as a tan/pink solid with a melting point greater than 250° C.

Example 6 illustrates the efficacy of compounds of the invention in inhibiting the viral helicase activity.

EXAMPLE 6

Assay for Helicase Inhibition

The helicase inhibition assay was performed according to methodology of the type described, for example, in: Lain et al., Nucleic Acids Res. 18:7003–7006 (1991); Warrener et al., J. Virol. 69:1720–1726 (1995); Kim et al., Biochem. Biophys. Res. Comm. 214:160–166 (1995). The value given in Table 1 represent the average of three test results in which the concentrations of anti-viral compound required to achieve a 50% inhibition of helicase activity ($IC_{50}$) were measured.

TABLE 1

| Example Number | $IC_{50}$ ($\mu M$) |
|---|---|
| 3 | 7 |

The relatively low concentration of the anti-viral compound of the invention required to achieve 50% inhibition of the viral helicase activity tends to show that the compounds of the invention are effective at interfering with propagation of HCV.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

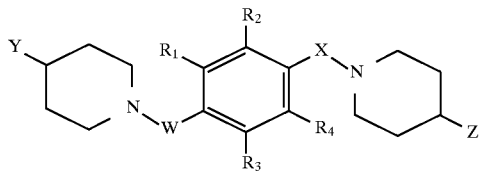

wherein $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; W and X represent the same or different linking moieties selected from the group consisting of alkylene ($C_1$–$C_5$) and carbonyl (—(C═O)—); Y and Z represent the same or different substituents selected from the group consisting of

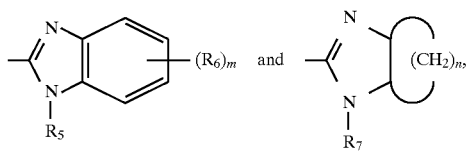

wherein $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and wherein $R_7$ represents a substituent selected from the group consisting of hydrogen, alkyl and acyl, and n is from 3 to 5; and the isomers and pharmaceutically acceptable salts of said compounds.

2. A compound having the formula

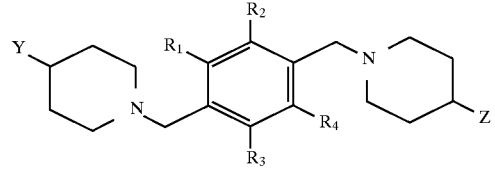

wherein $R_1$ R2, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; Y and Z represent the same or different substituent selected from the group consisting of

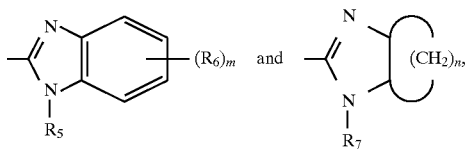

wherein $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and wherein $R_7$ represents a substituent selected from the group consisting of hydrogen, alkyl and acyl, and n is from 3 to 5; and the isomers and pharmaceutically acceptable salts of said compound.

3. The compound 1,1'-[1,4-phenylenebis (methylene)]bis (4,4'-trans-(4,5,6,7,8,9-hexahydro) benzimidazoyl) piperidine and the pharmaceutically acceptable salts of said compound, as claimed in claim 2.

4. The compound 1,1'-[1,4-phenylenebis( methylene)]bis (4,4'-benzimidazoyl) piperidine and the pharmaceutically acceptable salts of said compound, as claimed in claim 2.

5. A compound having the formula

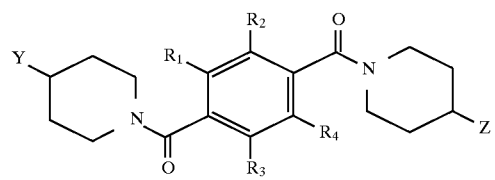

wherein $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; Y and Z represent the same or different substituent selected from the group consisting of

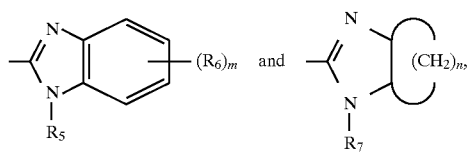 and 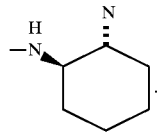

wherein $R_5$ represents a substituent selected from the group consisting of hydrogen, alkyl ($C_1$–C6) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4, and wherein $R_7$ represents a substituent selected from the group consisting of hydrogen, alkyl and acyl, and n is from 3 to 5; and the isomers and pharmaceutically acceptable salts of said compound.

6. The compound 1,1'-[1,4-phenylenebis (carbonyl)]bis (4,4'-benzimidazoyl) piperidine and the pharmaceutically acceptable salts of said compound, as claimed in claim 5.

7. A compound having the formula

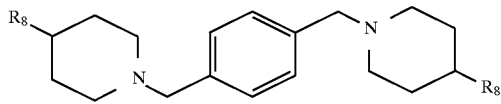

wherein $R_8$ represents a carbalkoxy ($C_1$–$C_6$) substituent.

8. A compound having the formula

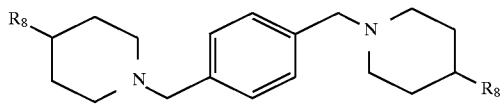

wherein $R_8$ represents

[structure]

9. A pharmaceutical composition for treating hepatitis C virus infection, said composition comprising a compound as claimed in claim 1 in an amount effective to attenuate infectivity of said virus, and a pharmaceutically acceptable carrier medium.

10. A composition as claimed in claim 9 in the form of a solid with a pharmaceutically acceptable excipient.

11. A composition as claimed in claim 9 in the form of a liquid with a pharmaceutically acceptable diluent.

12. A composition as claimed in claim 9 comprising from about 5 to about 50 mg of said compound by weight of said composition.

13. A method of treatment of hepatitis C virus infection in a patient in need of said treatment, said method comprising administering to said patient a therapeutically effective amount of a compound of claim 1.

14. A method as claimed in claim 13, wherein said compound is administered in unit dosage form containing about 5 to about 50 mg of said compound per kilogram of patient body weight per day.

15. A method as claimed in claim 14, wherein said unit dosage includes a pharmaceutically acceptable carrier medium.

16. A method as claimed in claim 13, wherein said composition is administered parenterally.

17. A method as claimed in claim 13, wherein said composition is administered orally.

* * * * *